United States Patent [19]

Ibar

[11] Patent Number: 4,469,649
[45] Date of Patent: Sep. 4, 1984

[54] METHOD AND APPARATUS FOR TRANSFORMING THE PHYSICAL CHARACTERISTICS OF A MATERIAL BY CONTROLLING THE INFLUENCE OF RHEOLOGICAL PARAMETERS

[76] Inventor: Jean-Pierre Ibar, Avenue de la Division Leclerc, Ballainvilliers (Essone), France, 91160

[21] Appl. No.: 287,673
[22] Filed: Jul. 28, 1971

Related U.S. Application Data

[63] Continuation-in-part of Ser. No. 129,767, Mar. 12, 1980, abandoned.

[30] Foreign Application Priority Data

Mar. 14, 1979 [FR] France .................... 79 06532
Feb. 6, 1980 [FR] France .................... 80 02620
Feb. 26, 1980 [FR] France .................... 80 04252

[51] Int. Cl.$^3$ ............................. B29F 3/00
[52] U.S. Cl. ......................... 264/23; 264/70; 264/237; 264/319; 425/174.2
[58] Field of Search ............ 264/23, 72, 70, 22, 264/348, 24, 27, 237, 319; 425/174.2

[56] References Cited

U.S. PATENT DOCUMENTS

| | | | |
|---|---|---|---|
| 2,408,627 | 10/1946 | Green | 264/70 |
| 3,113,829 | 12/1963 | Porter | 264/72 |
| 3,182,102 | 5/1965 | Simnad | 264/0.5 |
| 3,306,835 | 2/1967 | Magnus | 264/23 |
| 3,396,217 | 8/1968 | Foster | 264/27 |
| 3,597,794 | 8/1971 | Mann | 425/140 |
| 4,192,048 | 3/1980 | Robillard | 28/246 |
| 4,193,956 | 3/1980 | Kalnins | 264/27 |
| 4,198,461 | 4/1980 | Keller et al. | 428/288 |
| 4,252,513 | 2/1981 | Kalnins | 264/27 |
| 4,288,398 | 9/1981 | Lemelson | 264/23 |
| 4,349,502 | 9/1982 | Pae et al. | 264/320 |
| 4,399,083 | 8/1983 | Inoue | 264/23 |
| 4,403,069 | 9/1983 | Keller et al. | 264/23 |

OTHER PUBLICATIONS

"Vibro-Molding: A New Process to Mold Polymeric Materials", J. P. Ibar, ACS Polymer Preprints, vol. 21(1), pp. 215-217, (1980).
"Non-Newtonian Flow Characteristics of Amorphous Polymers in the (T Tg) Temperature Range", J. P. Ibar, ACS Polym. Prepr., vol. 21(1), pp. 218-219, (1980).
"Non-Linear Relaxation Behavior of Amorphous Polymers in Rubbery State", J. P. Ibar, ACS Polym. Prepr., vol. 21(1), pp. 220-221, (1980).
"Rheomolding: A New Process to Mold Polymeric Materials", J. P. Ibar, Polym.-Plast. Technol. Eng., vol. 17(1), pp. 11-44, (1981).
"Instability in the Rubbery State Revealed by D.S.C. of Rheomolded ® Polystyrene Samples", J. P. Ibar, Polymer-Communications, vol. 24, pp. 331-335, Nov. 1983.

Primary Examiner—Donald E. Czaja
Assistant Examiner—James C. Housel
Attorney, Agent, or Firm—Seidel, Gonda & Goldhammer

[57] ABSTRACT

The invention relates to a method and apparatus for transforming the physical characteristics of a material such as for an end finished molded product and to the materials or products obtained thereby. The method and apparatus are characterized in that the temperature of the material is simultaneously varied with at least one other rheological variable such as hydrostatic pressure, shear stress, mechanical vibration (frequency or amplitude), dielectric vibration (frequency or amplitude) for dielectric materials and electromagnetic properties for metallic materials. The variation in temperature and the simultaneous variation in one or more other rheological variables are intimately connected by a relationship selected and specifically programmed to obtain a product having improved properties.

16 Claims, 9 Drawing Figures

METHOD AND APPARATUS FOR TRANSFORMING THE PHYSICAL CHARACTERISTICS OF A MATERIAL BY CONTROLLING THE INFLUENCE OF RHEOLOGICAL PARAMETERS

CROSS REFERENCE TO RELATED APPLICATION

This application is a continuation-in-part of patent application Ser. No. 129,767 filed Mar. 12, 1980 now abandoned.

BACKGROUND OF THE INVENTION

1. Field of the Invention

The present invention relates to a method and an apparatus for transforming the physical characteristics of a material and particularly a method and apparatus for molding by vibration (either mechanical or electrical) to enable the control or modification of the physical properties of the molded materials, notably their mechanical and optical properties, as well as the novel materials so obtained.

2. Description of the Prior Art

Modern improvements in classical molding technologies include the control of certain fabrication variables during, or subsequent to shaping, in order to increase the end-use performance of the finished product. In such diverse operations as rotational molding, blow molding or thermoforming, shaping is applied to an already preformed material. This technique permits the incorporaof means to impart improved characteristics in the processing method by structuring the material morphologically.

Probably one of the most significant factors influencing the final end-use performance of a material is the rate at which it has been cooled through its thermokinetic transition temperatures, that is, its melting temperature or its glass transition temperature. For crystalline and semi-crystalline materials, the number, size, type and distribution of crystallites produced under specific cooling conditions dictate to a large extent the degree of crystalinity, density of the defects, if any, the importance of the amorphous regions as well as the overall morphology which determine the performance of the finished product. It is well known, for instance, that crystallites act as fillers or physical crosslinks in a polymeric system, and as such they play an important role in the determination of the shear modulus of the sodified product. Also it is known that the degree of crystallinity determines the optical aspect of the end-use article, controlling its transparency to light. Complete transparency is generally achieved under certain circumstances for crystallizable material under cooling conditions which avoid crystallization.

Therefore, one sees that the physical and physicochemical characteristics of a material depend on the speed or the variations in speed of cooling of the material during its passage between a molten or pasty state and a solid state.

Figure 1:
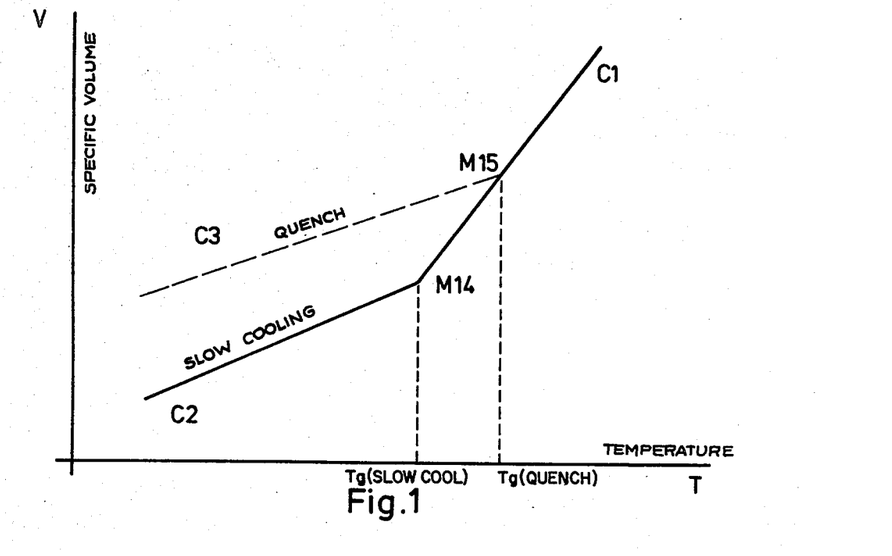
FIG. 1 is a graph illustrating the influence of the variation in the cooling speed on the final state of the material after cooling.

Amorphous non-crystallizable materials are materials able to condense into a glass, which is structurally similar to, but kinetically indistinguishable from, liquids. FIG. 1 depicts the volume changes as a glass-forming rubber is cooled through its glass transition temperature $T_g$. All glass forming materials undergo a drastic property change on passing through this region, the precise value of which depends on the rate of cooling and other experimental factors, e.g., pressure and time. The state of a glassy system is a nonequilibrium one, reflecting a frozen-in disordered condition with strongly restricted molecular mobility. It is seen in FIG. 1 that an amorphous material cooled rapidly through its $T_g$ condenses at a higher temperature and that the specific volume of the quenched glass is greater than that of the slowly cooled material. The physical properties of amorphous thermoplastics in the glassy state can vary considerably with the rate of cooling through $T_g$ (alternatively with subsequent annealing treatment below $T_g$), as is well known for the impact resistance of polycarbonate. Impact strength is the ability to dissipate the energy of an impact through some mechanical loss process without breaking of the material. The reason why unmodified amorphous polymers display such a large variety of impact behaviors, from the tough polycarbonate to the brittle polystyrene, is not well understood. Of all the unmodified amorphous polymers, polycarbonate has one of the highest values for impact strength. Yet, it has been reported that polycarbonate can completely lose its impact energy when it is extensibly annealed below its glass transition temperature. This same drastic loss of the impact characteristics of polycarbonate would be observed by cooling it slowly through its $T_g$ to permit relaxation under non-isothermal cooling conditions.

The existence of residual stresses in thermoplastics, due to forming assembly processes and to post-treatments, is a well known problem to design and applications engineers. Residual stresses can be enhanced by quenching and released by annealing below $T_g$. Once the residual stresses are formed, then the rate at which they relax is controlled by the ability of the material to recover to its equilibrium state. The residual stresses influence the optical and mechanical behavior of the engineered product since they contribute to the total stress level, therefore a knowledge of residual stresses, and means to control its level, are important when selecting the maximum allowable external stresses which can be applied to the thermoplastic article.

Another important influence on the rate of cooling is illustrated in the formation of compatible blends of materials. A polyblend is a blend of two or more substances. For instance, for macromolecular substances, a polyblend would be a mixture of chemically different powders, resins or elastomers. From both thermodynamic considerations and experimental observations, when polymers of different compositions are mixed they do not intermix down to the molecular level and therefore do not provide a homogeneous single-phase structure. The ultimate state of molecular mixing attainable by molecular mixtures can only be approached by polymeric polyblends up to a limit. Conceptually, compatability can be a representation of how close the polyblend approaches the ultimate state of molecular mixing as a limit. Hence, compatability can best be described by the degree of homogenity of the polyblend and measured and compared by the domain size of the dispersed phase. The thinner the size of the dispersed phase in the continuous phase, the better the compatability of the polyblend.

The compatability of a molten blend of two or more polymers is a function of temperature. The higher the temperature, the better the compatability. The perfection of compatability and its dependence on temperature and time are rate or diffusion sensitive processes—it is a function of the cooling rate imposed on the molten blend in the mold cavity while being cooled to room temperature.

A supercooled blend or a blend quenched at infinite rate would theoretically have the compatability characteristics it had at the temperature from which the quench started. Thus this is another important consideration on the effect of the cooling rate on the final characteristics of the finished product.

Thermal history during forming plays an important role in the determination of the properties of the end finished product. Therefore the ability to monitor the rate of temperature variation while the material is processed, in order to alter its properties, is a major technological objective.

Studies, carried out up to the present, in the laboratory, had consisted of working at constant hydrostatic pressure and modifying the cooling speed of the material by insulating the material or by accelerating its heat exchange to the outside.

Known methods consisting of modifying the heat exchange between the material in the course of cooling and the outside, are limited by the restrictions of heat transfer (conduction, convection, or radiation). Accordingly, it is not always possible to modify to a great extent the speed of heat exchange or the variation in temperature within sufficient limits to influence the physical characteristics of the end-finished molded product once it had reached ambient temperature.

The classic approach in metallurgy to the problem of obtaining non-equilibrium phases has been rapid removal of heat by convection. Generally, a molten metal is dropped into a cooling fluid, such as liquid nitrogen. With specimens, a few microns thick, cooling rates on the order of ten thousand or even twenty thousand degrees centigrade per second have been attained. Due to the poor heat conductivity of certain non-metallic materials, such as polymeric materials, special attention must be paid to simple size and geometry considerations in quenching experiments. While the extremely high cooling rates employed in metallurgy are not necessary in preparing completely amorphous polymeric samples, the technique can only be used on very thin samples and therefore industrial applications are indeed very limited.

Numerous materials are transformed today from an initial crude state to a finished or semi-finished article by molding operations. These materials are, for example, metals, glasses, ceramics, polymers, resins and rubbers; organic or inorganic; synthetic or natural. These materials can also be blends of several materials.

These materials are each endowed with a characteristic set of mechanical and physical properties which depend on its chemical nature, but which also strongly depend on its thermodynamic state after molding, in particular, the state of thermodynamic nonequilibrium at the temperature of use, which to a large extent depends on its thermal history during molding.

Various researchers have sought to modify and improve certain physical and mechanical characteristics of materials by controlling the parameters of the molding process. For instance, the influence of a constant hydrostatic molding pressure on the mechanical and relaxation properties of both amorphous and semi-crystalline polymeric materials have been the subject of extensive investigations.

Figure 2:
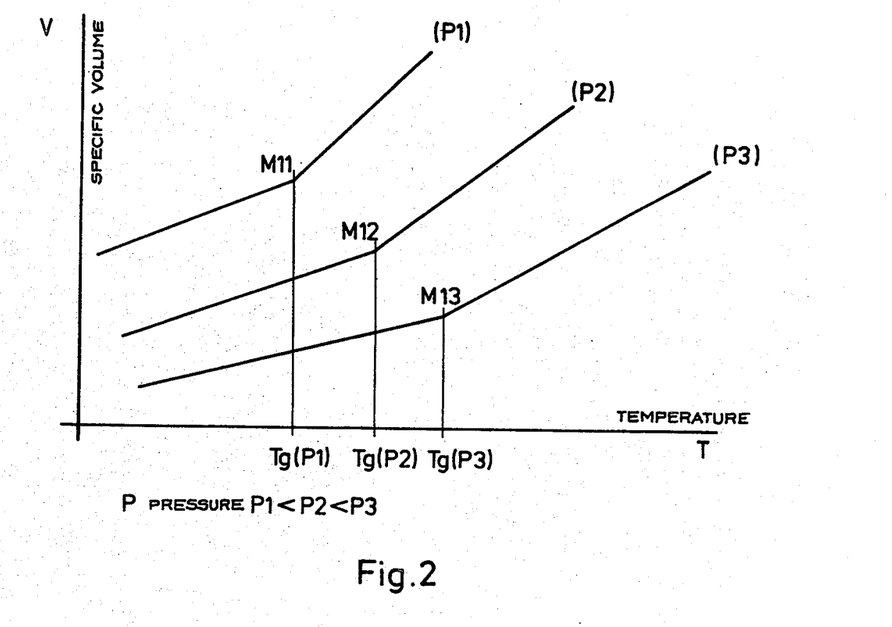
FIG. 2 is a graph illustrating the variation in specific volume as a function of temperature at various constant hydrostatic pressures.

It is known that a constant hydrostatic pressure applied during cooling modifies the change of state of materials, for example, in the vitrification process. This influence is manifested by the fact that the temperature of vitreous transition ($T_g$) is a function of the constant hydrostatic pressure exerted on the liquid material during cooling as shown in FIG. 2. The value of $T_g$ reflects the thermokinetic instability state of the vitrified material or glass. This signifies that it is theoretically possible to condense this material to the vitreous state at any temperature, on condition that a sufficient constant hydrostatic pressure is applied to raise the vitreous transition temperature ($T_g$) at least up to the temperature concerned. These phenomena have been described experimentally in the literature. See G. Allen et al., *J. Polymer. Sci.*, C, 23, 127 (1968), W. C. Dale et al., *J. Appl. Polymer. Sci.*, 16, 21 (1972), and E. Jones Parry and D. Tabor, *J. Materials Sci.* 8, 1510 (1973).

However, it is not suggested anywhere in these publications to vary the hydrostatic pressure during the cooling of the material in a manner which is controlled by the variation of the temperature of the material itself for the purpose of controlling or even "tailoring to order" the properties of the final end-use product.

The Bogulavsky et al. patent (U.S. Pat. No. 3,912,480) describes a method for annealing glass by bringing it to its annealing temperature (below $T_g$), maintaining it at this temperature in a fused salt bath, and subjecting it simultaneously to mechanical vibration of fixed frequency between 20,000–18,000 hertz, transmitted by the fused salt (whose viscosity does not exceed 100 hertz) to the glass. This method is not intended to cause a change in state and operates at a fixed frequency and temperature contrary to the present invention. Furthermore, it is only applied to mineral glass, without mentioning other materials.

U.S. Pat. No. 4,150,079 to Chang involves a method for controlling (suppressing or enhancing) crystallization in crystallizable thermoplastic polymeric materials by varying hydrostatic pressure during cooling. It is not suggested in Chang to apply vibrational means (either mechanical or electrical) superimposed on the action of the hydrostatic pressure to determine specific cooling patterns.

SUMMARY OF THE INVENTION

A method for modifying the physical and physicochemical characteristics of a material which comprises controlling the rate of a rate sensitive change of physical state of the material from an equilibrium state to a non-equilibrium state by simultaneously varying as a function of time at least two rheological parameters. The rates of change of the rheological parameters with time are controlled in accordance with a predetermined relationship to achieve an end product of prescribed physical and/or physicochemical characteristics. At least one of the rheological parameters is mechanical vibration, shear stress, hydrostatic pressure, dielectric vibration for dielectric materials or electromagnetic vibration for metallic materials. For crystallizable materials, the rheological variables include mechanical vibration, shear stress, dielectric vibration for dielectric materials, and electromagnetic for metallic materials. For non-crystallizable materials hydrostatic pressure is an additional rheological variable. Variations in vibration (mechanical, dielectric or electromagnetic) can either be by means of frequency or amplitude (intensity).

In varying the temperature and other rheological variables, the material passes through a rate sensitive transition involving a change of physical state such as between a solid, pasty or molten (liquid) state and a solid state, e.g., crystalline or amorphous for the cooling of a material. This phase transition is rate sensitive which means crossing it at a given speed would result in a specific non-equilibrium state.

The present invention can be utilized during operations on the material such as molding, heating followed by quenching, annealing, or any combination of these opera- tions.

More than one rheological parameter can be varied simultaneously with temperature. For example, vibrational treatment can be superposed on the action of a static stress.

Improved properties imparted to materials by use of the present invention include stress and strain under tension or flexion, elastic modulus, mechanical strength, flexibility, resistance to chemical corrosion, surface hardness, heat capacity, homogeneity, impact resistance and thermal conductibility. Furthermore, use of this invention can result in a modified level of crystallinity, a modified crystalline texture and a reduced annealing time to stabilize the material.

The pressure and vibration treatment of this invention can be applied uniformly over the whole outer contour of the molded material. In addition, said vibration treatment plus static force may also be applied in certain places of the contour around the molded material via bulges and cavities in the walls of the mold.

The treated materials may be initially in the form of particles, powders, blends, films, plates (laminar or not), or even "sandwich" type structures. The materials may be polymers, (synthetic or natural), ceramics, metals, glasses, rubbers, just to name a few.

This invention also relates to an apparatus characterized in that it is constituted by the combination of means enabling the material to be subjected simultaneously to a programmed cooling, and frequency vibration which can range up to 3000 or more cycles. This cooling may be accomplished either by convection with cold gas, or by wetting with water or other fluids.

The regulating device which programs the variation of the vibration characteristics of the apparatus can be adapted to enable the application of a constant frequency, a frequency varying logarithmically with time, or a frequency varying in programmed manner in harmony with the variation in temperature of the mold. This regulating device permits control of the level of vibratory force acting on the material (the force sine wave amplitude) according to a predetemined program which harmonizes the variation of the vibration force with the temperature of the mold.

The apparatus of this invention may include means for subjecting the material to the pressure of a gas or on the contrary to high vacuum in the course of the treatment. Further, the apparatus of the present invention can include means for applying a pre-determined thermal gradient to the material in the course of treatment, the gradient being applied in the direction of the thickness of the material. Thus, the apparatus of this invention can involve subjecting a material to a vibration whose characteristics (frequency and amplitude) are programmed in the course of cooling to achieve specific improvements of the end-finished product. The static force (non-oscillatory) applied to the material may vary in programmed manner. The vibration treatment (whose frequency and amplitude vary as programmed) enables the induction of oscillating forces on both sides of the average static stress. This vibration being applied at least from the moment where the temperature has reached its highest value and at the latest until the moment when the material is brought back to the selected temperature, for example ambient temperature. The vibration frequency and amplitude are programmed as a function of the cooling curve of the material, of the rheological nature of the materials, and of the changes which are desirable to be induced in the treated material.

Although the vibrations may be applied to the material in various ways, and, particularly, by mechanical means, this general solution, applicable in numerous cases, has the drawback of creating mechanical vibrations outside the apparatus. The vibrations of the frame of the apparatus are troublesome, because they fatigue the members of the frame assembly and therefore cause a severe maintenance problem for the apparatus.

The invention also involves the variation of dielectric vibrations to a material which has dielectric characteristics. In such a case, the material is considered as the dielectric of a capacitor (acting as a container) in that the dielectric and the material are subjected to a sinusoidal electrical field whose frequency and voltage intensity are determined as a function of time by a specific program. It is also possible to exert a programmed variation in time in the voltage and intensity of the nonperiodic electrical field in the case of a dielectric material. This variation is in harmony with the variation in the temperature of the mold.

It is not proposed to create in the material a release of heat to bring it to a certain temperature, but to cause the frequency of electrical excitation and the amplitude of the signal to vary, that is to say the intensity of the electrical current or the magnitude of the voltage across the capacitor, during the cooling of the material. In this way an internal visco-elastic state is generated which permits induction of specific cooling patterns.

The advantage of the application of vibrations of electrical origin, in the case of a material with dielectric properties, is to ensure the same modification of the physico-chemical characteristics of the material as in the case of vibrations of mechanical origin (since the curve, representing the log f (Hz) as a function of the reciprocal of the absolute temperature (1/T) which correspond to the visco-elastic transition, is a single curve, whatever the nature of the frequencies).

The advantage of this particular feature of the method, according to the invention, resides in the better energy yield of the operation, less fatigue in the equipment, reduction in the cost of the installation, more accurate control of the method as a function of a predetermined program (frequency and amplitude of the vibra- tions).

According to another feature of this invention, vibrations of mechanical origin and vibrations of electrical origin are applied simultaneously, for example, to condition several visco-elastic transitions during cooling. This enables account to be taken of the secondary transitions which always appear.

Finally, according to another feature of this invention, electrical vibration means are used to heat the dielectric material in place at constant frequency (resonance frequency), before application of the novel method of this invention.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

The graph of FIG. 1 shows the variation of the specific volume as a function of the temperature T at a given hydrostatic pressure, but at two different cooling speeds. The curve obtained is composed of two parts $C_1$ and $C_2$ which join at the transition point $M_{14}$. If the cooling is sped up, the change does not occur according to the curve $C_2$, but according to the curve $C_3$, starting from the point $M_{15}$. The transition is hence itself dependent on the variation in the cooling speed.

The curves of FIG. 2 show the variation of the specific volume (reciprocal of the density) of a material as a function of the temperature, when the material is subjected to three distinct constant hydrostatic pressures $P_1$, $P_2$, $P_3$ ($P_3 > P_2 > P_1$).

The three curves of FIG. 2 show distinctly that the variation in the specific volume is greater at high temperature, than at low temperature. The two parts of each curve at constant pressure join at a point defining the transition, respectively $M_{11}$, $M_{12}$, $M_{13}$, corresponding respectively to the transition temperatures $T_g (P_1)$, $T_g (P_2)$, $T_g (P_3)$. Hence it is possible to study the variation of the transition point by point of as a function of one rheological parameter, in this case $T_g$, as a function of the hydrostatic pressure.

Figure 3:
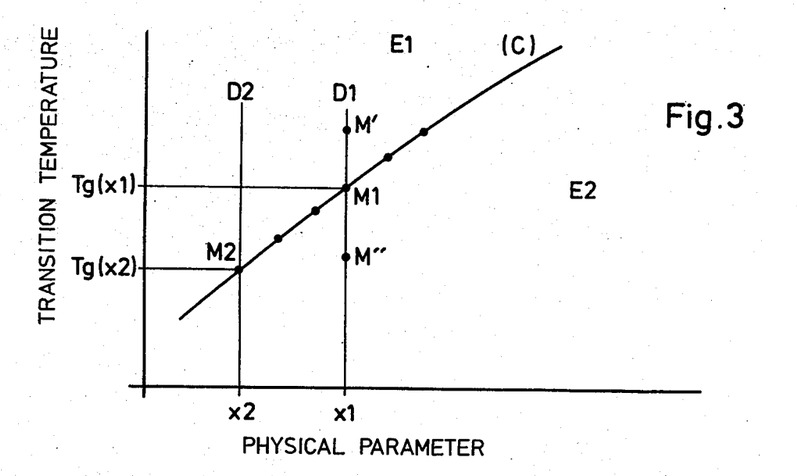
FIG. 3 is a graph demonstrating the variation of the transition temperature ($T_g$) as a function of a rheological parameter (x).

The graph of FIG. 3 is a plot of the transition temperature ($T_g$) between two physical phases $E_1$ and $E_2$ as a function of a rheological parameter (x), other than temperature. The subscript "g" in "$T_g$" refers to a particular case of a glass transition between phases $E_1$ and $E_2$. This transition temperature is the solidification temperature in the case of a crystallizable material solidifying according to a crystalline structure. This temperature may also be the vitreous transition tempreature in the case of a noncrystalline material. The transition temperature may further be any other transition of the secondary type in the case of a material having distinct physico-chemical particularities on each side of this secondary transition. Curve (C) is plotted point by point, the variable x kept constant and the specific volume versus temperature recorded to determine the transition temperature.

According to the graph of FIG. 3, the curve (C) separates two rheological states $E_1$ and $E_2$. In the region above the curve (C), the material is in a state $E_1$. Below the curve (C), the material is in the state $E_2$. For establishing the curve (C), the passage between the state $E_1$ and the state $E_2$ is made by remaining at a constant value of the parameter x, that is to say, moving on a line $D_1$ parallel to the temperature axis. This line $D_1$, corresponding to the parameter $x_1$, intercepts the curve (C) at the point $M_1$. At a point M', situated above the point $M_1$, the material is in the state $E_1$; at a point M", situated below the point $M_1$, the material is in the state $E_2$. The passage between the states M' and M" is affected by lowering the temperature.

The point $M_1$ corresponding to the transition can itself be dependent on the cooling speed (see FIG. 1), that is to say the speed at which the interval M', M" is traversed. Accordingly, it is necessary in order to fully program the variables of the method of this invention to include the curve families corresponding to the different cooling speeds.

In the majority of cases quoted in the literature, the rheological parameter is the hydrostatic pressure. Studies have also been carried out in laboratory to use vibration frequency as the rheological parameter (mechanical, electrical or electromagnetic), as well as the amplitude (or intensity) of the vibration. In these latter cases, the graph of the transition temperature versus the rheological parameter is of the same nature, as in FIG. 3, that is to say the curve separates the state $E_1$ distinctly from the state $E_2$ without showing a loop, a point of retrogression, etc. In FIG. 3, it is shown that the transition temperature increases as x increases. If, for a certain rheological variable chosen, this were not the case, x would represent the reciprocal of the rheological parameter.

Figure 4:
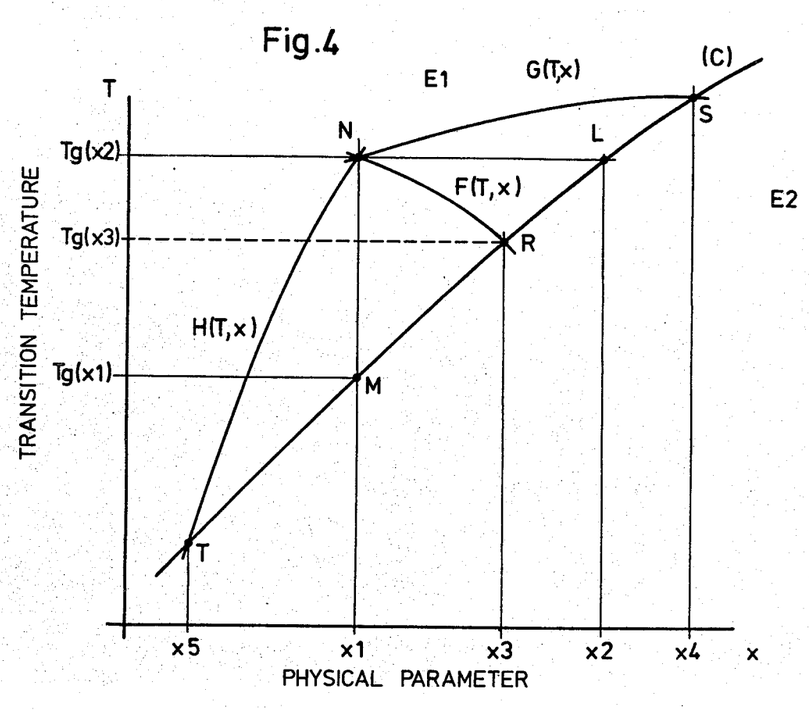
FIG. 4 is a general graph of the variation of $T_g$ as a function of x illustrating the method according to this invention.

FIG. 4 is a graph illustrating how to program the variation of the rheological variables as a function of the variation of the temperature in order to simulate the effect of specific cooling patterns during molding of a material according to the present invention.

According to this invention, to modify the speed of change in temperature on passage through the transition curve (C), that is to say to modify the speed of passage from the state $E_1$ to the state $E_2$, it is provided to connect the variation of temperature T and the variation of another rheological parameter x influencing the transition temperature in the vicinity of and during its change of state according to a function such as F (T, x), G (T,x) and H (T, x).

According to the prior art, the lowering of the temperature of the material which initially is in the state represented by the point M', is conducted while keeping the parameter x constant at the value $x_1$. The change of state occurs at $M_1$ along the vertical $D_1$ passing through the point M'. The speed of change in temperature which strongly affects the properties of the end-finished product is dependent only on the heat transfer with the mold.

According to the invention, the temperature T and the parameter x are varied simultaneously in order to induce novel physical characteristics due to the specific thermal history of the material once it has reached ambient temperature.

The variation of temperature and the parameter x can be harmonized according to the function F which is represented in FIG. 4 by a curve decreasing towards increasing x between the initial point N and the point of intersection R of the transition curve (C) corresponding to x$_3$.

The variation of temperature and the parameter x can also be harmonized according to the function G (T, x) in FIG. 4. The corresponding curve initiated at the point N intercepts the transition curve (C) at the point S, above the horizontal line passing through the point N and intercepting the curve (C) at the point L corresponding to x$_2$. The horizontal line NL corresponds to the formation of the state E$_2$ by the action of the rheological parameter x alone, the temperature remaining constant.

The variation of temperature and the parameter x can also be harmonized according to the function H (T, x) in FIG. 4, so that the representative curve passing through the point N intercepts the transition curve (C) at a point T, situated below the point M, that is to say corresponding to parameter x$_5$ (x$_5$<x$_1$).

In the first case, curve [F (T, x)], the temperature of the material diminishes before reaching the transition temperature Tg (x$_3$) at the point R, and simultaneously the parameter x increases which results in an accelerated approach to the state E$_2$. This case shows that the speed of approach to the state E$_2$ is controllable by means of the level of variation of the temperature T by heat transfer and also by means of the rheological variable x, the rate of which can be changed independently of the heat transfer. This case allows for simulation of the effects of a faster quench rate.

In the case of curve G (T, x) in FIG. 4, both temperature and parameter x increase at the same time. This indicates that the effect of an increase in temperature can be compensated by a simulataneous increase of Tg by the variation of x.

In the case of curve H (T, x) in FIG. 4, the temperature decreases at the same time as x decreases, the variation rates being independently programmable. This is particularly useful when the effects of rapid cooling, such as internal stresses, can be compensated by the simultaneous variation of x.

Generally, the parameter x can correspond to a physical magnitude or to the reciprocal of a physical magnitude.

Customarily, the rheological parameter x will be the stress (hydrostatic or shear, vibrational, non-vibration) and/or the vibration frequency, and/or the vabration amplitude to which the material will be subjected during its passage of the tansition curve.

Mathematically, the method of the invention can be analyzed by the partial derivatives.

In fact, if

Tg is the transition temperature of of the material
t the time
x a first variable capable of causing Tg to vary
y a second variable also capable of causing Tg to vary
then the variation in temperature as a function of time is written:

$$\frac{dT_g}{dt} = \left(\frac{\partial T_g}{\partial x}\right)_y \cdot \frac{dx}{dt} + \left(\frac{\partial T_g}{\partial y}\right)_x \cdot \frac{dy}{dt}$$

Approximately, in the vicinity of the transition point T$_{go}$ selected to correspond to the values x$_o$ and y$_o$ of the variable x and y, the following equation applies:

$$\left(\frac{\partial dT_g}{\partial dt}\right)_{(xo, yo)} = \frac{\partial [T_g(xo, yo)]}{\partial x} \cdot$$

$$\frac{\Delta x}{\Delta t} + \frac{\partial [T_g(xo, yo)]}{\partial y} \cdot \frac{\Delta y}{\Delta t}$$

Thus, the variation of Tg as a function of time t in the vicinity of a selected point of the curve (C) (or of the surface in the case of variables x and y) is controlled by modifying x and y as a function of time. The speed of approach to the state E$_2$ is a direct function of the variation of (dT$_g$/dt), and that of (dT/dt) which is controlled by heat transfer.

Now, if, by way of example, x is a pressure variable in time and y is a frequency variable in time, it suffices to program their variation in order to obtain the desired tion of (dT$_g$/dt)E$_1$→E$_2$. If there is only one one variable, for example x, one has necesarily ($\Delta y/\Delta t$)=0 and the formula giving dT$_g$/dt simplified.

The invention applies to any rheological parameter capable of acting on the transition temperature. Thus the invention is applicable to any parameter whose variation in time during the molding treatment is susceptible to simulate the effect of a cooling rate on the final properties.

Figure 5:
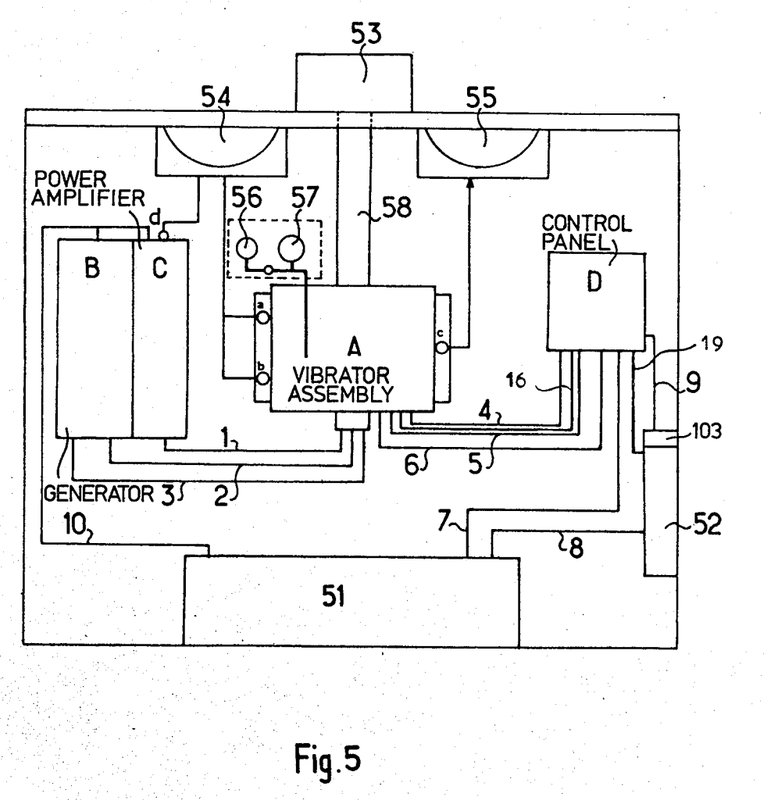
FIG. 5 is a representation in diagrammatic form of an apparatus of this invention.
Figure 6:
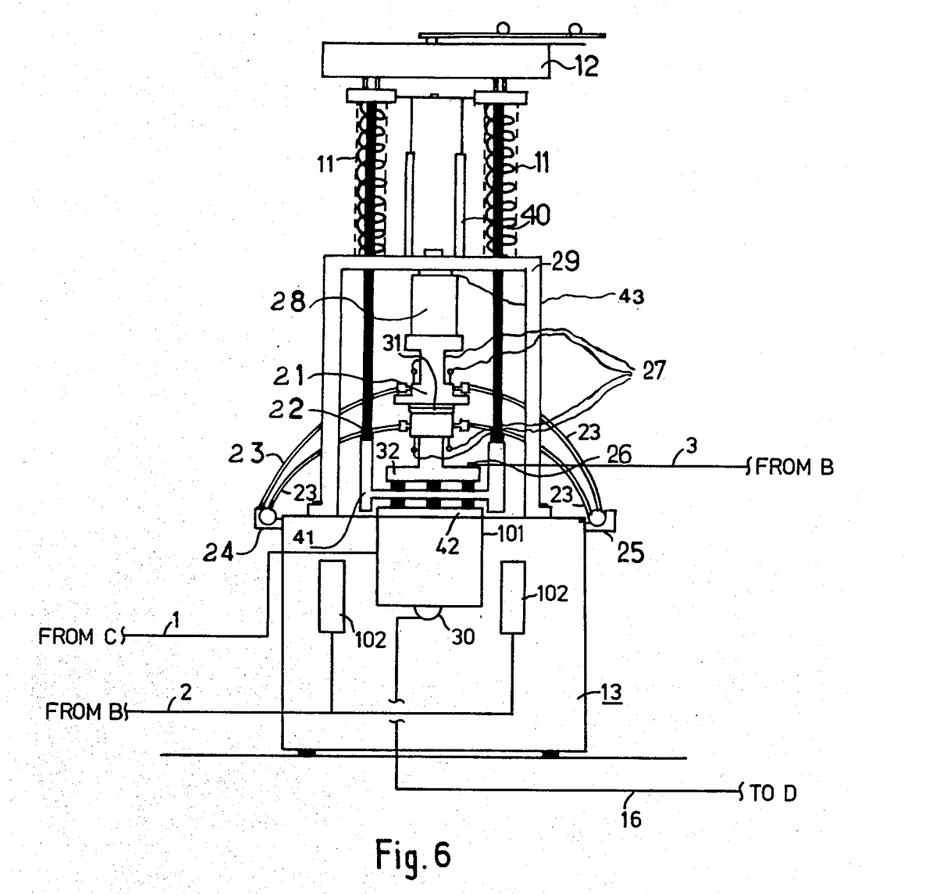
FIG. 6 shows in side view the apparatus designated as A in FIG. 5.

Referring to the drawings, the vibrator assembly which includes the mold is denoted by the letter A in FIG. 5 and is shown in detail in FIG. 6. The field supply of the vibrator and the vibration controls, such as a sine-wave generator, are shown at B, and are connected to a power amplifier C (solid state). A control panel D, enables the average applied force, the average displacement, the temperature and the degree of cooling to be monitored. The electrical energy is provided from the power amplifier C to the vibrator A through lead 1. Electrical leads going to the armature of the coil 101, to the field supply 102 and to accelerometer 26 are represented by 1, 2 and 3 respectively. The vibrator assembly A is connected to an air cooling turbine (blower) 53 through the pipe 58. The vibrator assembly A is connected via electrical leads 4, 5, 6 and 16 to the control panel D to enable the monitoring and regulating of the mean force, the force excursion, the phase difference between stress and strain and for measuring the displacement of the vibrating table 42 in FIG. 6. The vibrator 13 in FIG. 6 is connected to a cooling source, such as a belt-driven blower 53, to a coolant supply for both the amplifier and the mold at 54, and to a drain for the exit of the cooling fluid in 55.

A vacuum pump 56 including a manometer is connected to the mold (in A). A conditioning gas supply 57 is also connected to the mold (in A).

The connections to the heating elements (the heating elements are not shown—they are resistors or cartridges inserted within the mold halves 21 and 32) in FIG. 6, to the thermocouples 27, to the load cell 28, and to the element for measuring the displacement 30 are shown by 4, 5, 6 and 16 respectively. Electrical lines 7, 8 and 10 show the connections to the power supply, i.e., external electrical power. Connections 9 and 19 are used to carry the outputs to the chart recorders 52 and to the frequency or amplitude temperature function generator 103. It is possible to record the mean force, peak force, mean displacement, phase difference between force and displacement, temperature and frequency. Two valves, a and b control the cooling of the mold. Valve a enables the load cell and the vibrating table of the enclosure of the mold which is heated to be thermally isolated; valve b enables the cooling of the mold to be thermally conditioned. Valve c is an outlet valve for the cooling fluids. Valve d enables the cooling of the transistors of the power amplifier C to be adjusted.

Referring now more specifically to FIG. 6, the two parts of the mold 21 and 32 and the bellows 31, are placed between the load cell 28 and the support plate 41, itself screwed to the vibrating table 42. Threaded rods 22, pass vertically through the frame 29 and thus are screwed into the support plate 41.

The rotation of these rods 22 compresses the set of springs 11 and therefore applies force to the mold with a rate change which is controlled by the rotation speed of the rods. A mechanical device 12, controlled either manually (as in FIG. 6) or electrically by a motor, is positioned on a plate 40 which retains the springs 11, and enables a controlled pressure to be applied.

The cooling ducts 23 are connected to the mold through the input valves 24 (a and b in FIG. 5) and open into the outlet through the outlet valves 25 (c in FIG. 5). An accelerometer 26 is connected to the mold at 3, the thermocouples 27 and the heating elements (not shown in drawings). One of the thermocouples 27 is connected to the frequency - temperature generator B. The strain measuring element 30 is rigidly attached to the vibrating table inside the vibrator 13 and its output lead is connected to the control panel D in FIG. 5 through lead 16.

The machine is designed and constructed to be able to impart to the materials processed variation in temperature, stress (before the application of vibration) and vibration (frequency or amplitude).

A flexible metal bellows 31 allows for a small amount of relative motion between the upper and lower portion of the mold. The material to be treated is inserted between these two parts of the mold. Electrical heating elements are inserted in the two parts of the mold. Rapid or conditioned cooling of the mold is made possible by conduction of fluids in passages pierced in the mold close to the material to be processed.

An electromagnetic force energizer provides the vibrational motion which determines the total stress excursion exerted on the material.

The operating principle of the electromagnetic energizer is similar to that used in a high fidelity loud speaker, it being understood that in the present case the components are much larger and more powerful.

The load cell 28 is attached to the upper part of the mold 21 to enable the direct read out of the force exerted on the material located in the mold.

The other end of the load cell 28 is fastened to the frame 29 of the vibrator assembly A, itself screwed to the fixed armature of the vibrator 13. The output 43 of the load cell 28, is connected to a stress transducer which enables the force exerted on the material to be read directly. A selector switch enables either the average force developed on the specimen to be set (the mean of the sine-wave) or the peak force corresponding to the maximum compressive stress.

Frame 29 enables the armature of the vibrator A to be connected to the upper part of the mold through the load cell 28. It resists the forces of the armature of the vibrator 13 and exerts a retroaction on the body of the vibrator 13. The elastic modulus of the frame 29 is distinctly greater than that of the modulus of the material to be processed, which enbales the upper part of the mold to remain immobile.

So as to be able to maintain a compressive stress on the material despite the total vibrational stress imposed by the vibrator, a set of springs 11 are mounted above the mold and they enable relatively constant compressive stress to be exerted on the mold. This constant force is greater than a half-wave of the sinusoidal force. The forces exerted by the springs are read directly on the pressure gauge (in D).

Several thermocouples 27 are inserted in the mold as close as possible to the material (2mm) to be able to measure the temperature of the two parts of the mold. One of the outputs of the thermocouples is amplified and can serve as an input signal to the frequency and amplitude generator 103 of the vibration.

The output voltage of the other thermocouples is transmitted to an automatic instrument for regulating the temperature of the mold, and to a recorder y-t. This temperature regulator is provided with an electronic servo-regulator (proportional strip) for the electrical power delivered to the heating resistors. This device enables a desired temperature to be reached in a minimum time and to stabilize this temperature.

Depending upon the initial temperature in the mold, the amplitude and the frequency of vibration, the material being molded assumes specific physical states. In an apparatus according to the present invention, the mold cavity was so designed to compress plastic discs of various diameters and thicknesses, from about 2 mm minimum thickness to a maximum of about 3.75 mm with the widest diameter capable of molding being 70 mm. When discs of 70 mm diameter were used, the average platen pressure developed by the spring assembly was 450 psi produced by a total compressive force of 4140 pounds on a mean bellows area of 9.19 in$^2$.

The plastic was also capable of being heated to permit flow in the mold and in the bellows. It was therefore possible to submit flowing plastics or liquids to the process of vibration molding. The inserted mass could not exceed the mass of a PS disc with the following properties: 3.75 mm thick, 70 mm diameter, density about 1 g/cm$^3$. By means of flexible mechanical bellows, the material processed was capable of being heated to a temperature where it could flow into the cavity and the bellows. It was consequently possible to subject fused resins or even liquids to the vibration molding process of this invention. The amount of material introduced into the mold did not exceed 8.85 grams.

The amount of variable pressure which was developed by the force output from the vibrator varied according to the frequency at which the vibrator was operated. By calculation, it was estimated that an oscillating platen pressure of 225 psi would be attained at frequencies up to 200 Hz. Thus peak platen pressures of approximately 625 psi were attainable at frequencies up to approximately 200 Hz; the use of smaller samples permitted greater pressures to be attained.

The maximum displacement amplitude (at lowest frequencies) was 1.4 mm which corresponded to 40% of relative displacement for specimens of 3.75 mm initial thickness.

The vibrator was capable of operating at frequencies from 5 to 3000 Hz (with rapid excursions possible up to 5000 Hz). At frequencies above approximately 300 Hz, assuming constant amplitude of vibration, the force transmitted to the mold dropped off approximately inversely with the square of the driving frequency (Newton's formula of motion). The amplitude of vibration was capable of being lowered to preserve a constant output pressure even at the higher frequencies.

It was found empirically that the apparent moving mass of the machine, i.e., the force transmitted to the material divided by the acceleration, was frequency-dependent. The log of the moving mass was, in fact, linearly related (with a negative slope) to the log of the frequency. This indicated that the higher the frequency, the more difficult to transmit vibrational energy to the material. The mold temperature was capable of being set between 0° C. and 500° C.

The mold was capable of attaining the maximum temperature, 500° C., from room temperature in approximately less than 15 minutes. The mold was capable of being cooled in various cooling conditions. One of the most severe cooling conditions was quenching using water as the cooling agent and lowering the mold temperature from 500° C. to 60° C. in less than 2 minutes. The mold could also be heated or cooled with a flow of hot water (20° C.–70° C.). The mold could be cooled with a forced flow of gas, e.g., air or nitrogen, which allowed for a wide range of slow and controlled cooling rates.

The total mass (including the mass of the vibrating table) vibrated was about 60 pounds (27 kg). The apparatus used had a limiting capacity of 3,000 pounds (1363.64 kg) which could be provided by means of an acceleration of $(3000/60)=50$ g (g=the acceleration due to gravity, 9.8 m/sec$^2$).

The mechanical bellows which served as a vibrating enclosure had mechanical characteristics which could not be exceeded. In particular it could not be compressed beyond 0.055 inches (1.4 mm) when the flanges were not filled with material. On the other hand, when the material in fusion or the liquid filled the flanges of the bellows, the material communicated to the walls of the bellows its pressure and its variations in pressure. In this case the limiting value of the compression was only 0.035 inches (0.89 mm).

A solid state power amplifier was used as the main unit of the equipment. This delivered up to 8 KW of sine wave power at any frequency 5 Hz to 3000 Hz. The output modules (transconductors), of which there were four, each had 60 power transistors. These were driven by buffers and pre-amplifiers from a low level signal source (6 V RMS max.) to produce an output of 115 volts at 70 amperes. The load for this amplifier was the armature of the vibrator. This had a force rating of 3000 lb. It was air cooled by a motor driven centrifugal blower. The vibrator also required a source of direct current for the coil which created the intense magnetic field in the air gap. This was furnished by the field power supply. It had an output of 190 volts at 40 amperes.

The solid state power amplifier, the field power supply and the motor for the blower required 380 V, 50 Hz, 3 phase power. Total requirements amounted to approximately 28.3 KVA. This was supplied from the main power supply through a fused disconnect switch and a large 3 pole AC contactor on a wall adjacent to the equipment. Power for low level amplifier stages and control circuits was 110 V 50 Hz single phase supplied from an externally mounted control power transformer. Total 220 V power needed for the control cabinet equipment, the heaters, force and temperature measuring instruments was approximately 3 KVA.

The amplifier control panel, mounted integral with the power amplifier, provided push buttons, indicator lamps, safety interlocks, master gain control, etc. needed for the control of the power to the system.

The low level signal source was the sine wave control center. This was mounted in the same cabinet with the field power supply. It contained all circuits necessary for generating the low level AC signal, monitoring acceleration, velocity, amplitude, etc.

Cooling water was supplied to the heat sinks for the power amplifier transistor at a rate of approximately 3 gpm. Cooling water was also required for the mold on the vibrator. Air at approximately 38 lb/in$^2$ was required for the vibration isolation system of the vibrator.

Interconnection between the vibrator and the power amplifier and between the blower and the power amplifier was by means of cables for the blower (4 wires), field (2 wires), armature (2 wires), overtravel switches (3 wires) and accelerometer (coax.). Additional wires were needed for the mold heaters, the thermocouples, the load cell, the LVDT and the frequency generator.

The frequency and amplitude of vibration could be programmed during the molding process either according to a preset frequency-amplitude time pattern, or via a frequency-amplitude temperature converting electronic device. For this latter option, the millivoltage source from one of the thermocouples was continuously amplified and cold junction compensated before going to a "frequency-amplitude temperature converter" (F-A.T.C.).

The present frequency-time pattern or settings for the F-A.T.C. depended on the chemical nature of the material, the rheological behavior within the temperature range covered; and on the choice of the macroscopic property which it was desired to improve.

The control cabinet contained the circuits furnishing power to the mold heaters for the machine, a strip chart recording controller for mold temperature and a force measurement meter, used on conjunction with the load cell. Controls for this equipment were independent of the controls for the amplifier, which was also located in another cabinet.

Main power was obtained from 3 phase 380 V, 50 Hz lines through a 100 A main disconnect switch 1 DISC. Power at this voltage was used for the primaries of the transformer; for the power amplifier; power supply (for the armature) and the field power supply, as well as for the 3 HP motor used for the blower that cooled the vibrator.

Control power for the coils of the large contactors that switch line voltage power was 115 V, 50 Hz, single phase. This was obtained through a separate step-down transformer and fused disconnect switch.

Most of the control circuitry required 24 V DC to power small relays, solid state relay drivers (transistors) and for indicator lamps. It is obtained from the 115 V source by means of a step-down transformer, diode rectifiers and a filter capacitor.

Other circuits for solid state devices required 3 regulated ±15 V DC supplies, a +15 V DC zener regulated supply, a 24 V DC non-regulated supply and a 5 V zener regulated supply. Thus there are 6 separate DC supplies for control purposes.

The power amplifier power supply converted the 380 V, 3 phase, 50 Hz AC power to ±115 V DC with common. The field power supply converted the 380 V, 3 phase, 50 Hz AC to 190 V DC at 40 amperes.

Both of these supplies used step-down transformers and silicon power diodes in straightforward full wave bridge rectifier circuits. The power amplifier supply was exceptionally well filtered.

In order to illustrate the many practical advantages of the method, some non-limiting examples of the process according to the invention will now be described.

The effects of the vibrational treatment according to the invention on the physical properties of the molded materials is shown by the accompanying results of the measurement of these physical properties.

EXAMPLE 1

Figure 7:
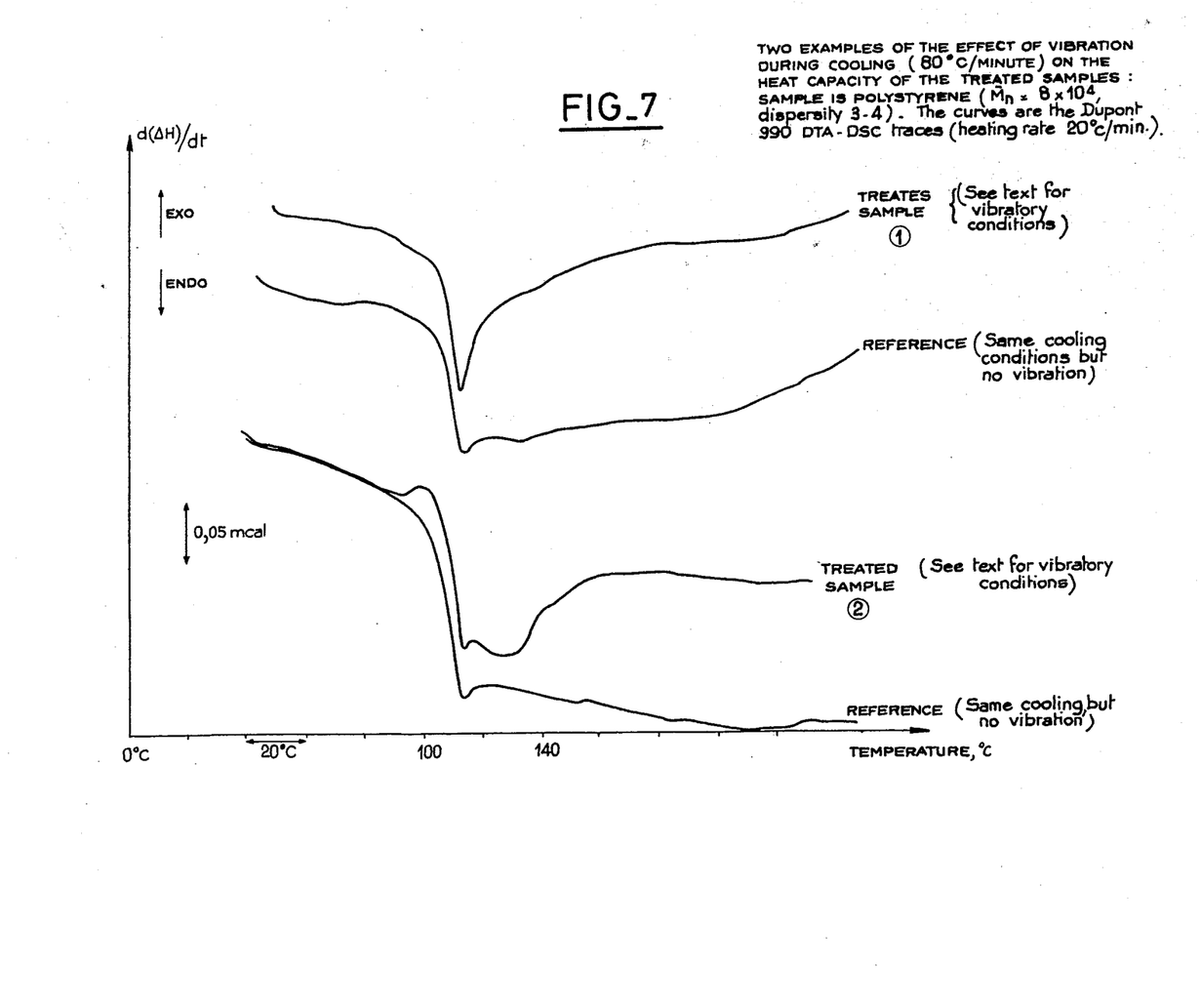
FIG. 7 is a graph showing the effect of a vibration molding treatment according to this invention on the heat capacity of a polystyrene.

With a Dupont-990 DSC cell, the effect of vibrational treatment on the heat capacity of a general purpose polystyrene material (PS) was tested. FIG. 7 gives the results for two different types of treatment. For each treatment, the reference curve corresponds to a sample cooled under the same conditions except for the vibration; hence, the reference curve corresponds to a classical compression molded sample. The heating rate was kept constant to 20° C./min. for all DSC runs.

In the treatment illustrated at the top of FIG. 7, the PS sample was initially a round piece of material sheet, it was placed in the mold and heated to ($T_g + 30°$ C.); i.e. 135° C. until the temperature held constant. A static pressure of 215 psi was applied on the sample; then vibration was switched on. The wave was initially 15 Hz, 0.005 inches peak to peak amplitude of deformation. When the mold was rapidly cooled in order to quench the sample, the frequency of vibration increased according to $f$ (Hz) = 15$e^{t/5}$, while the deformation amplitude remained constant. The vibrational treatment was interrupted when the temperature of the specimen reached 98° C. The specimen continued to cool down but the vibration was discontinued.

The reference sample of FIG. 7 (top curve) was cooled under the same conditions but the vibration was not applied during cooling. The thermograms of the treated and untreated samples clearly illustrate the differences in heat capacity of the two samples. Whereas the treated and untreated samples both exhibited a classical endotherm at the glass transition temperature, their post-transition thermal behavior was quite distinctive. The heat capacity of the treated sample reverted, after the $T_g$ endotherm was passed, to a value which was approximately equalled the extrapolated heat capacity (at the corresponding temperature) of the low temperature ($T < T_g$) behavior.

Thus, the sample which has been vibro-molded had thermal characteristics at room temperature (after the treatment) which could be extrapolated from the post $T_g$ behavior where it is known that the polymer is at equilibrium. This means that the treated sample behaved below $T_g$ like a sample which had reached equilibrium, i.e. like a specimen which has been extensively annealed.

Figure 8:
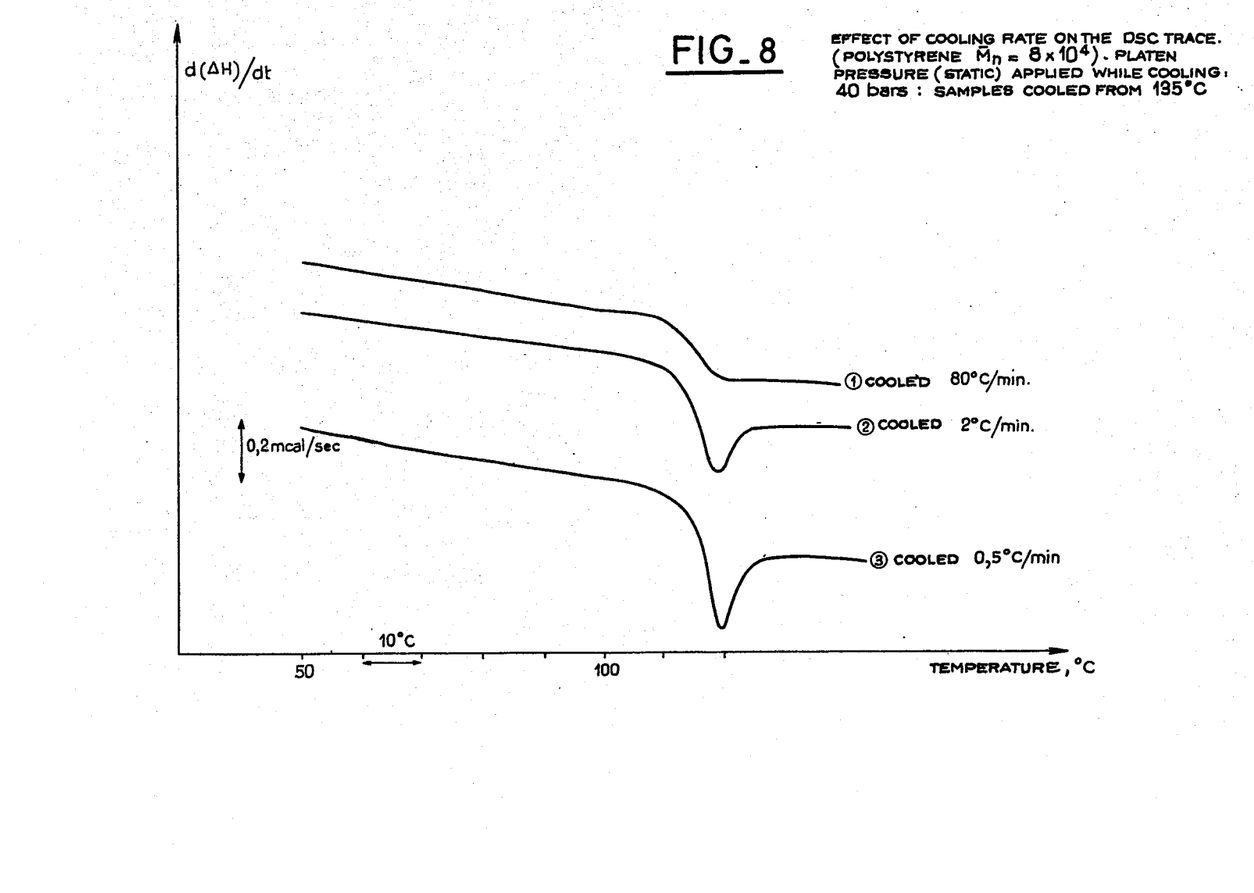
FIG. 8 is a graph showing the effect of the rate of cooling on the thermal properties of atactic polystyrene.

The heat capacity of the untreated sample (the reference specimen) leveled off beyond the endotherm showing a large heat capacity difference between the glassy ($T < T_g$) and the rubbery state ($T > T_g$). This behavior is typical of a quenched material, as further illustrated in FIG. 4. In this figure, a PS sample was cooled under 580 psi static pressure, at three different cooling rates (80° C./min, 2° C./min, 0.5° C./min). The initial temperature in the rubber state was 135° C. It is clear that the vibromolded specimen of FIG. 7 (top) behaved like a slowly cooled sample (bottom trace of FIG. 8), whereas it had in fact been subjected to a severe quenching process.

This Example therefore demonstrates that the vibrational treatment according to the invention applied during cooling permits control and improvement of the state of equilibrium, i.e., the stability of the "glass" formed without losing the advantage in speed of a quenching process. The method also permits the elimination of lengthy and costly post-quenching thermal treatments (such as annealing) which are currently used to relieve the "glass" from the internal stresses built up and frozen therein during the quenching operation.

EXAMPLE 2: Effect On Mechanical Properties Of Treated Samples

The second treated sample of FIG. 7 was another polystyrene sample quenched from the rubbery state at 80° C./min. while vibration was applied. The static pressure acting on the specimen was 217 psi; the initial temperature was 120° C. The frequency of vibration during cooling was constant at 100 Hz. The sinusoidal pressure was $P = 217 \pm 126 \sin(2\pi \times 100\, t)$, where P is in psi, t is time in seconds. The vibration was interrupted when the temperature of the sample reached 80° C. FIG. 7 (lower curves) shows the DSC thermograms of the "vibro-molded" (molding in accordance with this invention) sample and of a reference specimen cooled identically, but with no vibration during cooling. Once again, the thermal behavior of the treated and untreated samples were different. The endothermal characteristics at $T_g$ were more complex for the treated than for the untreated sample. In particular, the endotherm was broad for the treated material, extending over a 40° C. range. The mechanical properties in tension and flexion of the treated and untreated specimens were investigated using a procedure conforming to ASTM D790 (I) and ASTM D638-68.

(1) Flexion results:

| | Treated Sample: |
|---|---|
| Flexural Strength: | 13635 psi |
| | (disperson: 5%) |
| Maximum strain %: | (4.2 ± 0.2) % |
| Modulus in flexion: | 400350 psi |
| | (dispersion: 5%) |
| | Untreated Sample: |
| Flexural strength: | 1096 psi |
| | (dispersion: 4%) |
| Maximum strain %: | (2.7 ± 0.3) % |
| Modulus in flexion: | 386000 psi |
| | (dispersion: 6%) |

(2) Tensile Test:

| | Treated Sample: |
|---|---|
| Tensile strength: | 6100 psi |
| | (dispersion: 7%) |
| Percentage elongation at break: | 2.4–3% |
| Yield stress: | 4540 psi |
| | (dispersion: 2%) |
| Percentage elongation at yield: | (1.6–2) % |
| Modulus in tension: | $3.75 \times 10^5$ psi |
| (dispersion: | 5%) |
| | Untreated Sample: |
| Tensile strength: | 5080 psi |
| | (dispersion: 5%) |
| Percentage elongation at break: | (1.5–2) % |
| Yield stress: | no yield point but ultimate stress |
| Percentage elongation at yield: | no yield point but ultimate stress |

| | |
|---|---|
| -continued | |
| Modulus in tension: | 1.6 × 10⁵ psi (dispersion: 5%) |

These results were obtained with a statistical population of four samples per treatment. The dispersion was one hundred times the ratio of standard deviation and mean average.

It is seen from the above results that the mechanical properties of the vibro-molded samples are superior, especially with respect to strength and percentage elongation. In flexion, for instance, the flexural strength of the vibro-molded sample was 35% greater and the ultimate strain 50% greater than the corresponding values for the untreated sample. This was also true, to a lesser degree, for the tensile results.

This example again shows that the specimen subjected to the above vibrational treatment during cooling was mechanically superior to the untreated specimen, especially in flexion.

EXAMPLE 3: Effect On The Ease Of Deforming Materials

The purpose of this example was to show that vibrational treatment applied to a glassy polymeric material below its glass transition temperature softens the material in a favorable manner.

Figure 9:
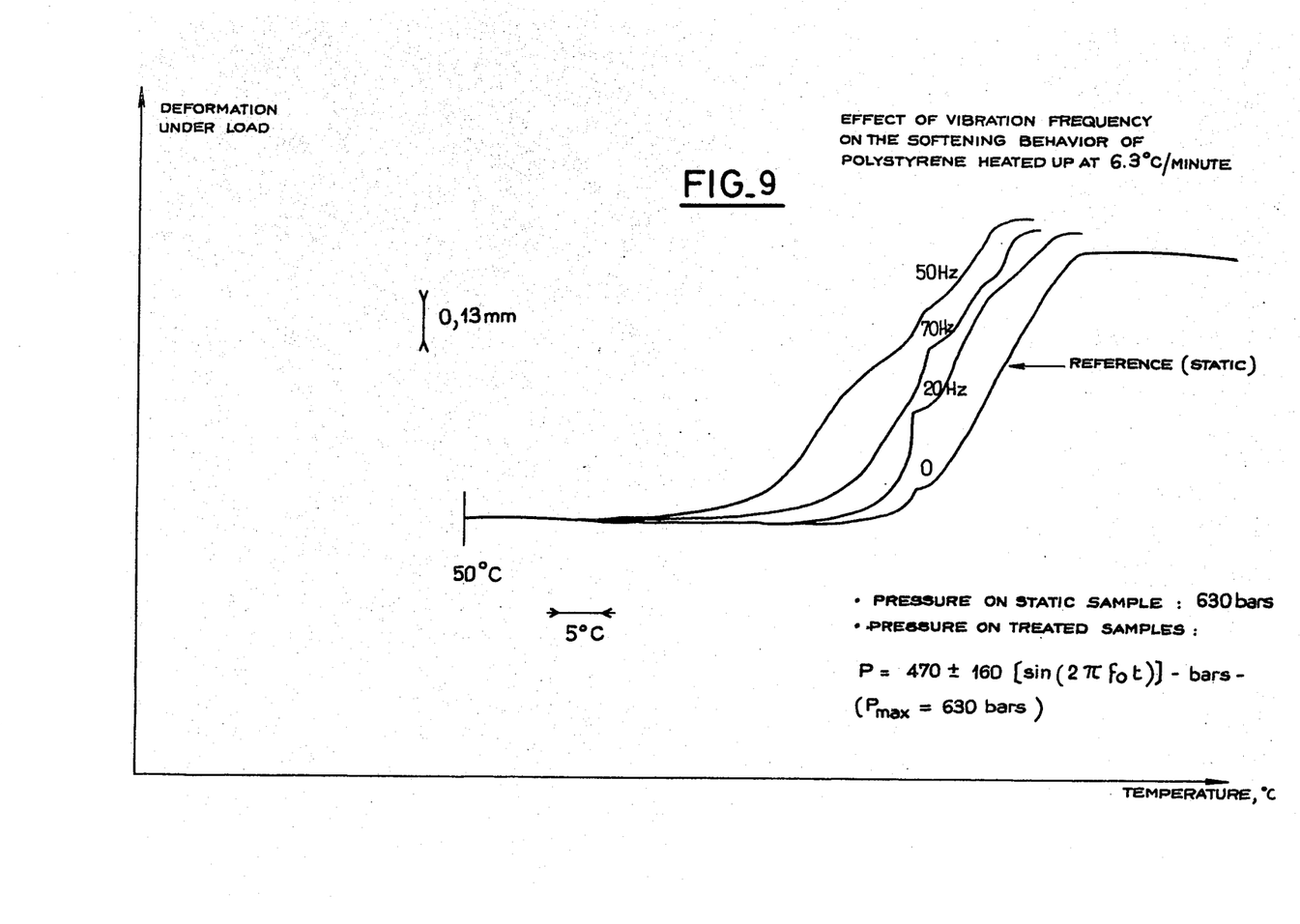
FIG. 9 is a graph showing the effect of various vibration frequencies at constant amplitude on polystyrene.

The material studied was a general purpose polystyrene already cut into disc-shaped specimens from sheet material. The untreated sample, which served as a reference, was pressurized at room temperature to 9140 psig platen pressure (the sample was allowed to flow laterally). Heat was applied to the mold in order to obtain a linear increase of the sample temperature. The deformation parallel to the force axis was measured and plotted against temperature in order to characterize the softening behavior of the material under static load. The treated samples were subjected, from 50° C. onwards, to an oscillating pressure $P = 6819 \pm 2321 \sin(2\pi f_o t)$ where P is in psi, $f_o$ is frequency in Hertz, t is time in seconds; the heating rate was identical for each sample. FIG. 9 compares the deformation-temperature curves of the samples pressurized statically and dynamically. For all samples the maximum pressure was the same, namely 9140 psi.

The average pressure acting on the treated specimens was 6819 psi, i.e. 34% less than the reference pressure. FIG. 9 shows the effect of vibration frequency on the softening temperature (the frequency remained constant during a run). It is clear from FIG. 9 that vibration applied during heating has a considerable influence on the ability to deform the material under load. For instance, the softening temperature was about 30° C. lower for the sample vibrated at 50 Hz. Hence, less dynamic pressure was needed to obtain the same deformational result. FIG. 9 also indicates that the frequency effect at constant average or maximum pressure is not straightforward. There seems to be a maximum of yield when the frequency during treatment is around 50 to 60 Hz. In any case, for mechanical treatments involving low temperature thermoforming ($T < T_g$), the advantages of using vibration at a chosen frequency during the process are quite clear, namely that a lower total pressure or a lower operational temperature can be used.

EXAMPLE 4: Reduction of Birefringence and of Thermal Stresses after Forming

The material used in this example was again a general purpose polystyrene, cut into disc-shaped specimens from a 2 mm thick sheet. The reference sample, was heated through its glass transition temperature to 140° C. A platen pressure of 8700 psi was applied at the corresponding temperature and the mold was fast quenched. The specimen changed dimensions during the process and it became reduced in thickness and increased in diameter. It was optically transparent, but the transparency was poor, the transmission of light being uneven. Examination of the specimen between cross-polarizers showed a birefringence (refraction of light in two slightly different directions to form two rays) pattern of radial symmetry (maltesecross isoclinic and concentric isochromes). The treated sample was geometrically identical with the reference. It was heated under no load to the same temperature 140° C. A dynamic 3 platen pressure of $6525 \pm 2175 \sin(2\pi \times 100 \, t)$ psi was applied and the mold was fast quenched as before. The vibration was interrupted when the sample temperature reached 50° C. The specimen was subjected at each cycle to the same total pressure, 8700 psi, as the reference pressure. The optical properties of the speciment were excellent. There was no birefringence pattern in the plane of the deformed disc. The specimen when viewed between cross-polarizers was totally black.

It was concluded that vibrational treatment during cooling permits the relaxation and elimination of thermal stresses and/or orientational stresses due to the thermomechanical treatment. The optical properties were improved by the vibrational treatment.

EXAMPLE 5: Compression Molding of Granules with Vibration

The polystyrene granules used are obtainable from the Dow Chemical Company (PS-lot S-108).

Reference samples (Ref. A) are prepared according to the following steps:
(1) 8.85 grams of granules were packed at room temperature into the mold cavity.
(2) The mold was heated rapidly to 210° C. in 7 minutes. During this time, a $4 \times 10^{-2}$ torrs vacuum was applied to the mold cavity.
(3) 435 psi of platen pressure was applied to the mold (1 minute).
(4) The mold was held at 210° C. for 1 minute, 3 minutes, and 5 minutes, respectively.
(5) The mold halves were quenched to room temperature with cold water. Pressure was removed when the sample temperature reached 50° C.

Another series of reference samples (Ref. B) were prepared according to the following steps:
Steps (1) and (2): as described above.
(3) 435 psi pressure was applied when the mold reached 100° C. and held at that pressure level.
Steps (4) and (5) as described above. Treated samples were prepared according to the following:
Steps (1) and (2) as described above.
Then when the sample temperature was 100° C., vibrational treatment was applied to the mold according to the following conditoins:
- Lower frequency limit: 5 Hz
- Upper frequency limit: 3000 Hz

- Sweep time from lower limit to upper limit: 30 seconds
- The vibration frequency cycled between 5 Hz and 300 Hz, the logarithm of frequency varied linearly with time.
- The mean pressure applied to the mold was 325 psi.

The mold was then quenched when the sample temperature reached 210° C. and vibration was stopped when the sample temperature reached 50° C.

In the following table are recorded the total time elapsed in the mold and the final appearance of the samples, with regard to the presence of bubbles.

|  | Reference Samples A | | | Reference Samples B | | | Treated Samples |
|---|---|---|---|---|---|---|---|
|  | 1 | 2 | 3 | 1 | 2 | 3 |  |
| Total time | 10 min | 12 min | 15 min | 10 min | 12 min | 15 min | 9 min |
| Bubbles | Many | Some | None | Some | Bubbles | None | None |

It is clear that vibrational tretament during molding enhances the diffusion of bubbles to the periphery and their subsequent pumping off from the mold by the vacuum device. The total time elapsed in the mold is much shorter to obtain satisfactory samples when the treatment according to the invention is applied.

The present invention may be embodied in other specific forms without departing from the spirit or essential attributes thereof and, accordingly, reference should be made to the appended claims, rather than to the foregoing specification, as indicating the scope of the invention.

1. A method for modifying the physical and physicochemical characteristics of a material which comprises controlling the rate of a rate sensitive change of physical state of the material from an equilibrium state to a non-equilibrium state by simultaneously varying as a function of time at least two rheological parameters, the rates of change of said rheological parameters with time being controlled in accordance with a predetermined relationship to achieve an end product of prescribed physical and/or physicochemical characteristics, wherein at least one of the rheological parameters is mechanical vibration, shear stress, hydrostatic pressure, dielectric vibration for dielectric materials or electromagnetic vibration for metallic materials.

2. The method of claim 1 wherein said variation in mechanical vibration and dielectric vibration include variation of amplitude.

3. The method of claim 1 wherein said variation of mechanical vibration and dielectric vibration include variation of frequency.

4. The method of claim 1 wherein said variation in dielectric vibration includes variation of voltage.

5. The method of claim 1 wherein machanical vibration and dielectric vibration are applied simultaneously.

6. The method of claim 1 wherein a static stress is simultaneously applied in addition to said vibrational treatment.

7. The method of claim 1 wherein said modification of characteristics occurs during a molding operation.

8. The method of claim 1 wherein said material is a polymer.

9. A method for modifying the physical and physicochemical characteristics of a material which comprises controlling the rate of a rate sensitive change of physical state of the material from an equilibrium state to a non-equilibrium state by simultaneously varying as a function of time both the temperature and at least one other rheological parameter, the rate of change of temperature with time and the rate of change of such other rheological parameter with time being controlled in accordance with a predetermined relationship to achieve an end product of prescribed physical and/or physicochemical characteristics, wherein the other rheological parameter is mechanical vibration, shear stress, hydrostatic pressure, dielectric vibration for dielectric materials or electromagnetic vibration for metallic material.

10. The method of claim 9 wherein said variation in mechanical vibration and dielectric vibration include variation of amplitude.

11. The method of claim 9 wherein said variation in mechanical vibration and dielectric vibration include variation of frequency.

12. The method of claim 9 wherein said variation of dielectric vibration includes variation of voltage.

13. The method of claim 9 wherein mechanical vibration and dielectric vibrations are applied simultaneously.

14. The method of claim 9 wherein a static stress is simultaneously applied in addition to said vibrational treatment.

15. The method of claim 9 wherein said modification of characteristics occurs during a molding operation.

16. The method of claim 9 wherein said material is a polymer.

* * * * *

UNITED STATES PATENT AND TRADEMARK OFFICE
CERTIFICATE OF CORRECTION

PATENT NO. : 4,469,649

DATED : September 4, 1984

INVENTOR(S) : Jean-Pierre Ibar

It is certified that error appears in the above—identified patent and that said Letters Patent is hereby corrected as shown below:

On Page 1, Position 22, delete "Jul. 28, 1971".

On Page 1, Position 22, insert --Jul. 28, 1981--.

Signed and Sealed this

Seventeenth Day of June 1986

[SEAL]

Attest:

DONALD J. QUIGG

Attesting Officer

Commissioner of Patents and Trademarks